(12) United States Patent
Hermansson et al.

(10) Patent No.: US 11,369,525 B1
(45) Date of Patent: Jun. 28, 2022

(54) SENSING PANEL FOR HYGIENE MONITORING DEVICE

(71) Applicant: Essity Hygiene and Health Aktiebolag, Gothenburg (SE)

(72) Inventors: Kent Hermansson, Gothenburg (SE); Anders Jonsson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/621,492

(22) PCT Filed: Jul. 5, 2019

(86) PCT No.: PCT/EP2019/068064
§ 371 (c)(1),
(2) Date: Dec. 21, 2021

(87) PCT Pub. No.: WO2021/004598
PCT Pub. Date: Jan. 14, 2021

(51) Int. Cl.
*A61F 13/42* (2006.01)
*A61F 13/53* (2006.01)
(Continued)

(52) U.S. Cl.
CPC .............. *A61F 13/42* (2013.01); *A61F 13/53* (2013.01); *A61F 13/5611* (2013.01);
(Continued)

(58) Field of Classification Search
CPC ................. A61F 13/42; A61F 2013/424; A61F 2013/8473
See application file for complete search history.

(56) References Cited

U.S. PATENT DOCUMENTS 5,181,905 A * 1/1993 Flam ...................... A61L 15/56
  374/161
5,291,181 A   3/1994 Deponte
(Continued)

FOREIGN PATENT DOCUMENTS

WO    2012166765 A1   12/2012
WO    2016090492 A1    6/2016

OTHER PUBLICATIONS

International Search Report (PCT/ISA/210) and Written Opinion (PCT/ISA/237) dated Mar. 17, 2020, by the Swedish Patent Office as the International Searching Authority for International Application No. PCT/EP2019/068064.

*Primary Examiner* — Catharine L Anderson
(74) *Attorney, Agent, or Firm* — Buchanan Ingersoll & Rooney PC

(57) ABSTRACT

A flexible sensing panel includes a flexible substrate having first and second major surfaces, first and second separated side edges, and first and second ends, the flexible substrate being at least partly disposed between a flexible protective layer and a flexible fastening layer, and at least one sensing element being disposed on the flexible substrate. The protective layer is secured to the first major surface of the flexible substrate and is folded over the first and second side edges onto the second major surface of the flexible substrate and secured thereto to position at least part of the first and second side edges within the so formed folds, and wherein the fastening layer is at least partly disposed on the second major surface of the flexible substrate and secured thereto.

20 Claims, 4 Drawing Sheets

(51) Int. Cl.
  *A61F 13/56* (2006.01)
  *A61F 13/62* (2006.01)
  *G01N 27/12* (2006.01)
(52) U.S. Cl.
  CPC ...... *A61F 13/625* (2013.01); *A61F 2013/424* (2013.01); *A61F 2013/530649* (2013.01); *G01N 27/121* (2013.01)

(56) References Cited

U.S. PATENT DOCUMENTS

| | | | |
|---|---|---|---|
| 9,675,503 B2 * | 6/2017 | Carney | A61B 5/207 |
| 10,383,564 B2 * | 8/2019 | Meek | A61B 10/007 |
| 2004/0207530 A1 | 10/2004 | Nielsen | |
| 2018/0333306 A1 | 11/2018 | Ahong et al. | |

\* cited by examiner

SENSING PANEL FOR HYGIENE MONITORING DEVICE

TECHNICAL FIELD

The present disclosure relates to a flexible sensing panel for a hygiene monitoring device and to a hygiene monitoring device comprising such flexible sensing panel.

BACKGROUND

A hygiene monitoring device may be used to monitor a hygienic state of a user, for example by monitoring the state of an absorbent hygiene article worn by the user. For example, a hygiene monitoring device may be used to detect the presence of and/or to determine the amount of body fluids absorbed in an absorbent hygiene article, such as a diaper or similar product, in order to monitor the development of the hygienic state. For example, the information acquired from such monitoring device may alert a caregiver or parent that the diaper needs to be changed or may be used as an assessment tool for developing a nursing plan.

It has been proposed that the hygiene monitoring device should be reusable in order to minimise the creation of waste. It has also been proposed that the hygiene monitoring device should be able to monitor the hygienic state of the user without direct contact between the device and the monitored entity. This is especially desired in the case of monitors for use with hygiene absorbent articles, in order to reduce the need for cumbersome cleaning efforts due to soiling of the hygiene monitoring device with for instance urine or feces.

Hygiene monitoring devices for absorbent hygiene articles, that are intended to be placed on an exterior, garment facing surface, of the absorbent hygiene article, and to be reusable, has therefore been proposed, see e.g. WO 2016/090492.

There remains, however, a need for improved reusable hygiene monitoring devices that are cost efficient in production, that are robust enough to be used multiple times and that provide an acceptable comfort when worn.

SUMMARY

It is desired to provide a reusable hygiene monitoring device that is cost efficient in production, is robust enough to be used multiple times and provide an acceptable comfort when worn. Sensing panels for use in hygiene monitoring devices according to the features of claim 1 at least in part meets this desire. Variations of the disclosure are set out in the dependent claims.

In one aspect, the present disclosure relates to a flexible sensing panel for a hygiene monitoring device, comprising a flexible substrate extending along a longitudinal direction and a transversal direction and having first and second mutually opposite major surfaces in the plane of the longitudinal and transversal direction, first and second mutually opposite, longitudinally extending and transversally separated side edges, and first and second mutually opposite, longitudinally separated edges.

The flexible substrate is at least partly disposed between a protective layer and a fastening means layer. At least one sensing element is disposed on the flexible substrate.

The protective layer is flexible and disposed on and secured to the first major surface of the flexible substrate and is folded over the first and second longitudinally extending side edges onto the second major surface of the flexible substrate and secured thereto to position at least part of the first and second longitudinally extending side edges within the so formed folds.

The fastening means layer is flexible and at least partly disposed on the second major surface of the flexible substrate and secured thereto.

By arranging a protective layer on at least part of the first major surface of the flexible substrate, the portions of that surface covered by the protective layer is protected against wear, such as scratches, that may otherwise cause damage to the sensing elements or other components on the flexible substrate. The protective layer may also provide a desired surface texture and appearance that could otherwise not be provided by the flexible substrate Folding the protective layer material over the longitudinal edges of the flexible substrate and securing the folded-over portions of the protective layer material on the second major surface of the flexible substrate may have several beneficial effects.

The longitudinal edges of the sensing panel, formed when folding the protective layer over the longitudinal edges of the flexible substrate, may be perceived as soft and non-abrasive as the folding of the protective layer creates a curvature at the edge formed by folding the protective layer material.

The folding-over of the protective layer may prevent entry of undesired substances, such as water, body fluids and/or dirt into the sensing panel structure. Such undesired substances may result in damage to and malfunction of the sensing panel.

The folding-over of the protective layer may provide a flexible sensing panel that has a low tendency of forming permanent creases in the flexible sensing panel after being bent. During use, the flexible sensing panel may need to be bent to form a curve in order to fit the exterior surface of the absorbent hygiene article on which the panel is intended to be secured. Also, during further use, removal and storage, the panel may be bent. In order for the sensing panel to be used and reused many times before disposal, it is advantageous that formation of permanent creases and folds in the sensing panel resulting from it being used is kept low. The above-mentioned combination of features provides a robust sensing panel that withstands the forces it is subjected to during use and that can be reused many times.

In addition to being folded over the longitudinally extending side edges, the protective layer may also be folded over at least one of, or both, the first and second longitudinally separated edges of the flexible substrate onto the second major surface thereof and secured thereto, in order to also make the longitudinally separated ends soft, non-abrasive, protected and/or resistant to creases.

The folded-over portions of the flexible protective layer and the flexible fastening means layer may together cover the full second major surface of the flexible substrate. By this, also the second major surface of the flexible substrate may be protected from mechanical wear, such as scratches.

The first and second longitudinally extending side edges of the flexible substrate may be positioned within the folds along at least 50% of their extension in the longitudinal direction. Stated differently, the flexible protective layer may be folded over the longitudinally extending side edges of the flexible panel along at least 50% of the longitudinal extension of the side edges. While it may not be necessary that the full length of the longitudinally extending side edges are positioned within the folds, it may be advantageous that this is the case for at least 50, 60, 70 or 80% of the longitudinal extension of the side edges, even though it may of course be possible that it may be the case for up to 100, 95 or 90% of the longitudinal extension of the side edges.

On the flexible sensing panel, the at least one sensing element may be disposed at a distance from the longitudinally extending, transversally separated side edges and optionally also from the longitudinally separated edges. The folded over portions of the protective layer may then preferably not be superposed on the at least one sensing element, i.e. such that no part of folded over portions of the protective layer overlies any portion of the sensing element.

It may be important that the protective layer is not covering the sensing elements, as this may lead to an impairment of the sensing performance.

The folded over portions of the protective layer may at least partly be disposed between the fastening means layer and the flexible substrate. In other words, the fastening layer material may extend transversally and optionally longitudinally into the area of the folded-over portions of the protective layer and is secured to that surface of the folded over portions that face away from the flexible substrate. By such arrangement, the fastening material layer may constitute a large percentage of that surface of the flexible sensing panel. Also, by arranging the fastening means layer on top of the folded-over portions of the protective layer, the edges of the protective layer are not exposed.

The protective layer may be secured to the flexible substrate by means of an adhesive, such as a pressure sensitive adhesive, to enable easy attachment of the protective layer to the surfaces of the flexible substrate.

The protective layer may be made from a liquid impermeable material, in order to provide a water-proofing the flexible sensing panel.

The protective layer may be made from a foam material to provide a soft feel and a flexible material.

The protective layer may have a thickness of from 0.1 to 1 mm, such as measured with an ordinary Vernier caliper without compressing the material.

The fastening means layer may comprise mechanical fasteners, such as hooks, disposed on a backing layer for enabling repeated securement to and removal from a surface, such as for example a surface of fibrous non-woven.

At least two longitudinally or transversally spaced apart sensing elements may be disposed on the flexible substrate. This may enable the sensing panel to function in a hygiene monitoring device adapted to detect the presence of or measure the amount of body liquids absorbed in an absorbent hygiene article by means of measuring the impedance between the two sensing elements, as is inter alia described in the afore-mentioned patent application WO 2016/090492.

The flexible sensing panel may be elongate along the longitudinal direction, i.e. having an extension that is larger along in the longitudinal direction than along the transverse direction. The ratio of the longitudinal length to the transversal width of the flexible sensing panel may be 5:1 or higher, such as from 5:1, 8:1 or 10:1 to 100:1, 50:1 to 25:1. This would for instance be suitable for a sensing panel intended to be secured on a garment facing surface of an absorbent hygiene article, such as a diaper, with the longitudinal extension of the sensing panel aligned along the front-to-back direction of the absorbent hygiene article, meeting a requirement of covering a certain proportion of the front-to-back distance while simultaneously fit the gap between the wearers thighs.

A data logger unit or a connector for removable attachment of data logger unit may be disposed on a portion of the first major surface of the flexible sensing panel, and the data logger unit/connector for removable attachment of the data logger unit may be electrically connected to the at least one sensing.

The flexible sensing panel may be adapted for being secured, preferably removably secured, to a garment facing surface of an absorbent hygiene article by means of the fastening means layer.

In another aspect, the present disclosure relates to a hygiene monitoring device, comprising a flexible sensing panel as described above, and a data logger unit removably attachable to the sensing panel and electrically connectible to the sensing adapted for detecting the presence of and/or quantifying the amount of body fluids absorbed by an absorbent hygiene article to which the hygiene monitoring device is associated.

DETAILED DESCRIPTION

Different aspects of the present disclosure will now be described more fully hereinafter with reference to the enclosed drawings. The embodiments disclosed herein can, however, be realized in many different forms and should not be construed as being limited to the aspects set forth herein.

It is to be understood that the drawings are schematic and that individual components are not necessarily drawn to scale.

Figure 1:
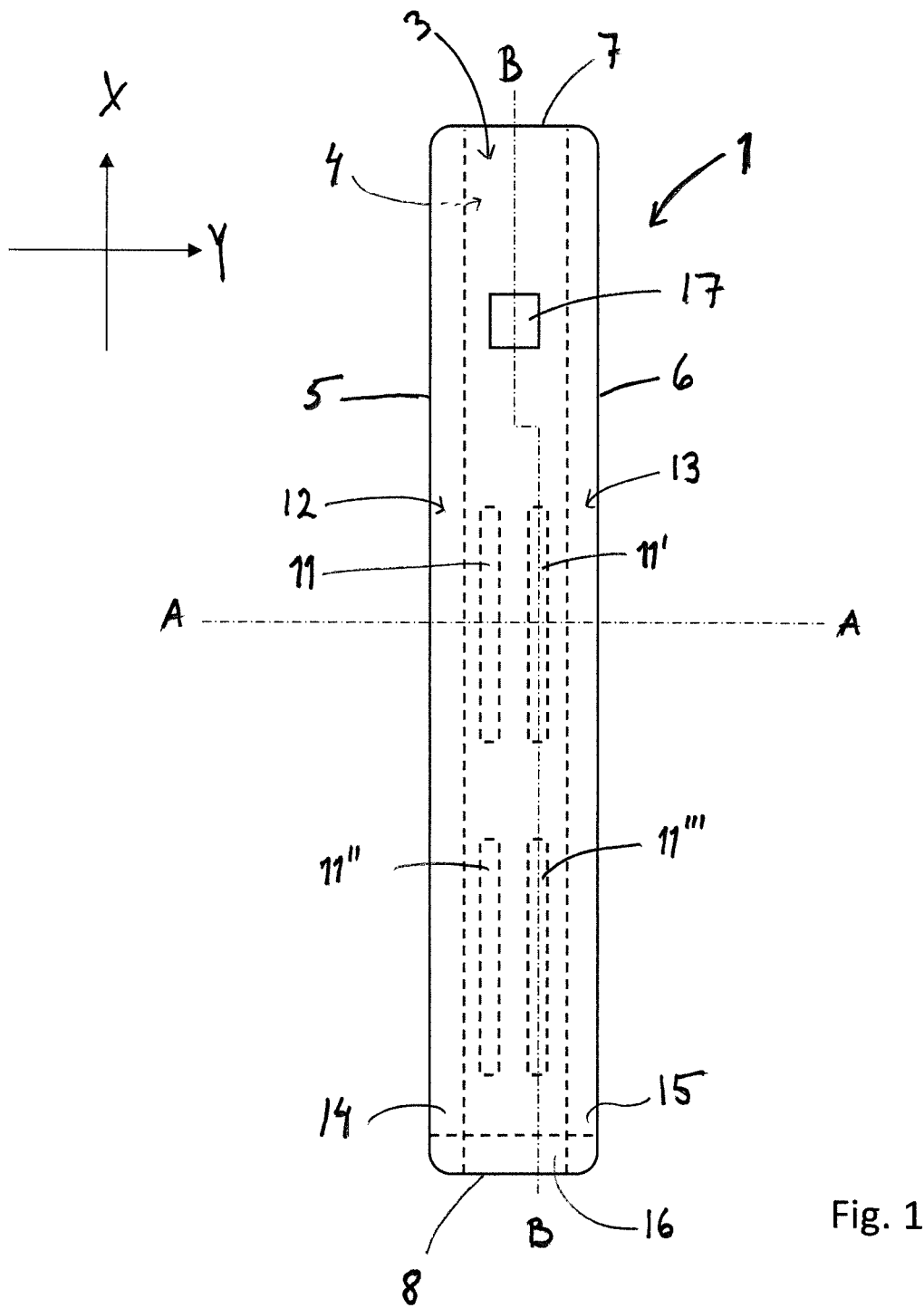
FIG. 1 is a schematic top view of a sensing panel
Figure 2:
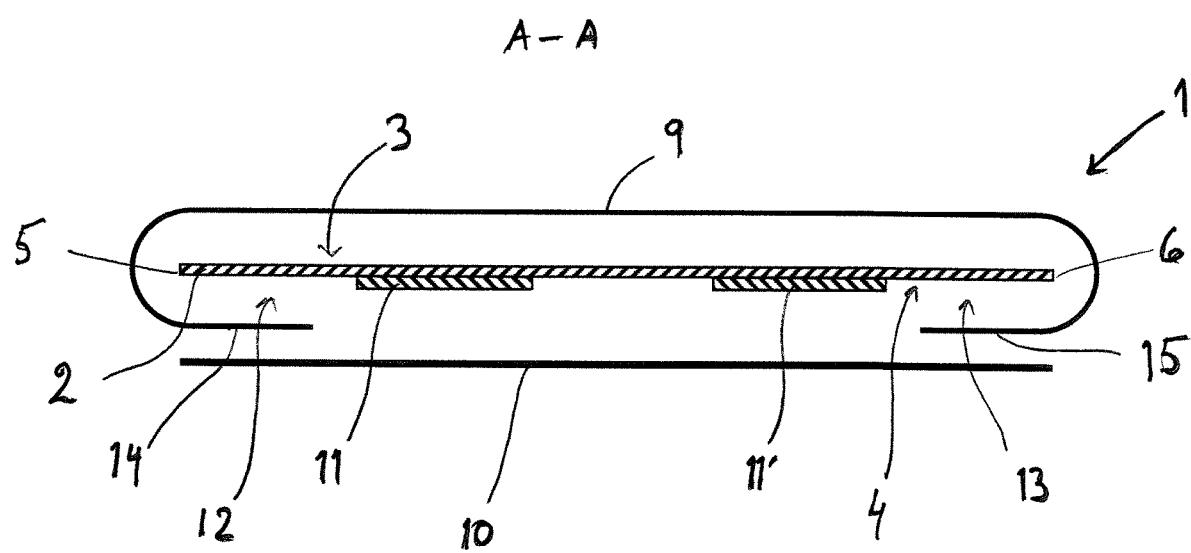
FIG. 2 is a schematic cross-sectional view of the sensing panel in FIG. 1, along the line A-A
Figure 3:
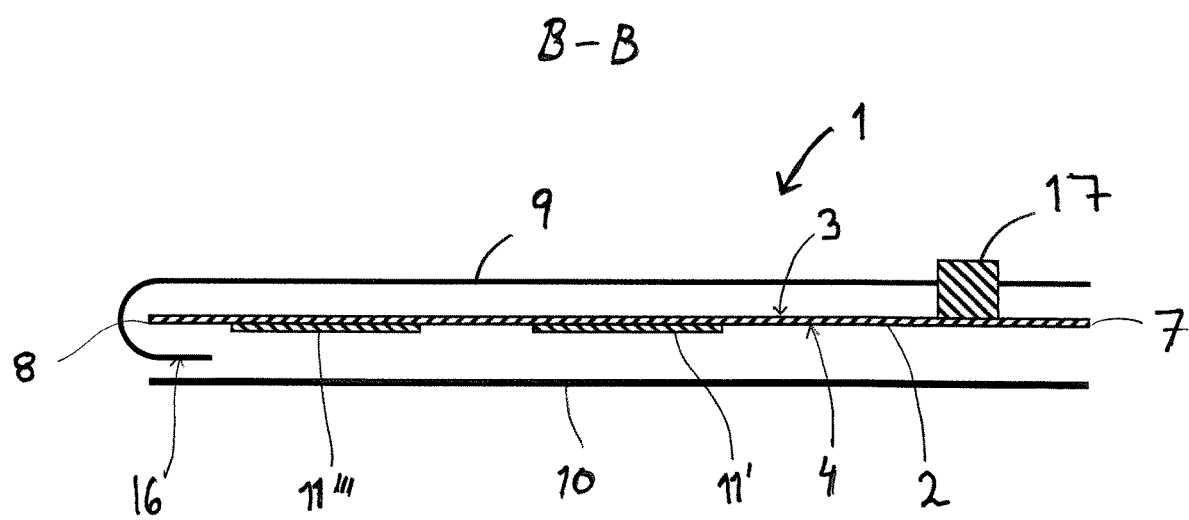
FIG. 3 is a schematic cross-sectional view of a sensing panel in FIG. 1, along the line B-B

An exemplary flexible sensing panel 1 for use in a hygiene monitoring device is shown in FIGS. 1, 2 and 3.

Figure 4:
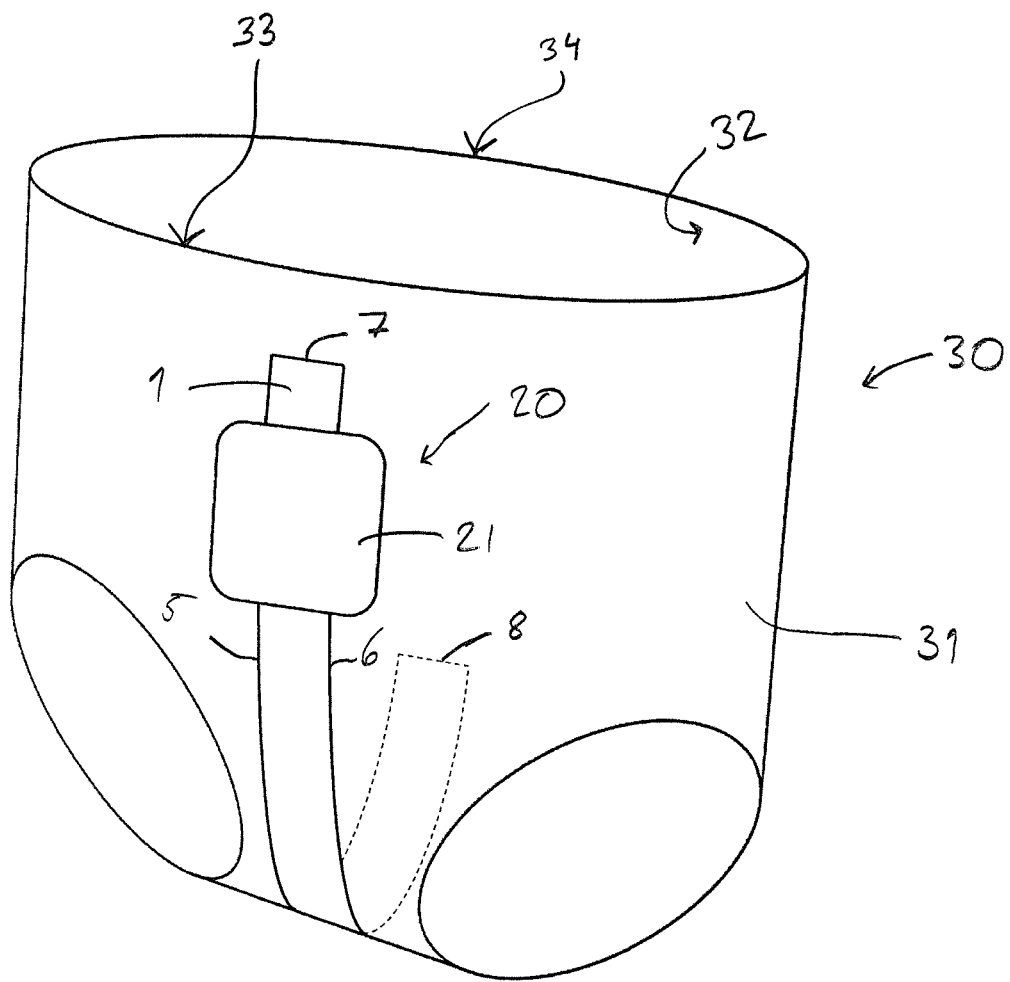
FIG. 4 is a schematic illustration of a hygiene monitoring device secured to an absorbent article

A hygiene monitoring device 20, comprising a data logger unit 21 connected to a flexible sensing panel 1, and attached to a garment facing surface 31 of an absorbent hygiene article 30 is schematically shown in FIG. 4.

The flexible sensing panel 1 comprises a flexible substrate 2 that extends in a longitudinal direction X and a transversal direction Y and presents two mutually opposite, transversally separated and longitudinally extending side edges 5, 6, and two mutually opposite, longitudinally separated edges 7, 8.

As is illustrated in FIG. 1, the flexible sensing panel may have two generally straight, parallel longitudinally extending side edges 5, 6. The longitudinally separated edges 7, 8 may be straight and parallel, giving the sensing panel 1 an essentially rectangular appearance, possibly with rounded corners. Alternatively the longitudinally separated edges 7, 8 may be rounded.

The flexible substrate 2 is an essentially two-dimensional material, i.e. its thickness in the direction orthogonal to the plane of the longitudinal direction X and the transversal direction Y may be essentially negligible in comparison to longitudinal length and its transversal width, respectively, so as to define a first and second, mutually opposite major surfaces 3, 4 of the flexible substrate in the plane of the longitudinal direction X and the transversal direction Y.

As illustrated in FIG. 4, the flexible sensing panel 2 may be adapted to be secured on the absorbent hygiene article 30 on the garment facing surface 31 thereof, i.e. the surface of the absorbent hygiene article 30 intended to face away from the wearer when in use, and that is opposite of the body facing surface 32 of the absorbent hygiene article 30. The flexible sensing panel 2 may be adapted to be secured with its longitudinal direction aligned to the front-back direction of the absorbent hygiene article, i.e. with one of the longitudinally separated edges 7 i.e. the front edge, towards the front waist edge 33 of the absorbent hygiene article 30 and the other one of the longitudinally separated edges 8, i.e. the rear edge, towards the rear waist edge 34 of the absorbent article 31, and the transversally separated, longitudinally extending side edges 5,6 aligned along the front-back direction of the absorbent hygiene article 30.

The thickness of the flexible substrate may be 2 mm or less, such as from 0.05, 0.075 or 0.1 to 2, 1 or 0.5 mm.

The flexible substrate 2 may be elongate along the longitudinal direction, i.e. d it may longer in the longitudinal direction than it is wide in the transversal direction. The ratio of the longitudinal length to the transversal width of the flexible sensing panel may suitably be 5:1 or higher, such as from 5:1, 8:1 or 10:1 to 100:1, 50:1 to 25:1.

The longitudinal length of the flexible substrate 2 may be from 10, 15, 20, 25 or 30 to 100, such as 80, 60 or 40 cm.

The transversal width of the flexible substrate 2 may be from 1, such as from 1.5 or 2, to 5, 4 or 3 cm.

The flexible substrate 2 has four sensing elements 11, 11', 11", 11''' in the form of conductive plates disposed thereon and in electrical contact with a connector 17 disposed on the first major surface 3 by means of conductive leads disposed on the flexible substrate (not shown). While in FIGS. 2 and 3, the sensing elements 11, 11', 11", 11''' are illustrated as being disposed on the surface of the flexible substrate 2, the sensing elements may also, within the scope of this disclosure, be integrated in the flexible substrate 2. The function of the sensing elements 11, 11', 11", 11''' and the connector 17 will be further described below.

The substrate 2 can be of any flexible material suitable for having sensing elements disposed thereon. The flexible substrate 3 may for example comprise a polymeric substrate, such as such materials commonly known to those skilled in the art as being suitable substrates for flexible printed circuit board (flex-PCBs), such as, but not limited to PI (polyimide) film, PET (polyester) film, PEN (polyethylene naphthalate) film, PTFE (polytetrafluoroethylene) film and Aram id film.

The flexible substrate 2 is at least partly disposed between a protective layer 9, and a fastening means layer 10. In order for the resulting sensing panel 1 to be flexible, the respective materials for the protective layer 9 and the fastening means layer are themselves flexible, i.e. readily bendable along at least one direction.

The protective layer 9 is disposed on and secured to at least part the first major surface 3 of the flexible substrate, and the fastening means layer 10 is disposed on and secured to the second major surface 4 of the flexible material 2.

The protective material 9 is, in addition to being disposed on and secured to the first major surface 3, folded over the longitudinal edges 5, 6 of the flexible substrate 2 and the folded over portions 14, 15 of the protective material 9 is secured to the second major surface 4 of the flexible material 2. In that way, the side edges 5, 6 of the flexible substrates are positioned within the folds 12, 13 formed by the folding over of the protective layer 9.

For instance, a piece of protective layer material 9 having a transversal width larger than the transversal width of the flexible substrate 2 may be attached to at least part of the first major surface 3 of the flexible substrate 2 with free edge portions of the protective layer material 9 extending transversally beyond the side edges 5, 6 of the flexible substrate 2. Thereafter, the free edge portions may be folded over the side edges 5, 6 of the flexible substrate 2 and secured to the second major surface 4 of the flexible substrate 2. The free edge portions that are folded over the side edges 5, 6 represent, after folding, the folded-over portions 14, 15.

The free edge portions of the protective material layer 9 may (before being folded over the edge of the substrate) extend from 1, 2, 3 or 4 to 10, 8 or 6 mm beyond that side edge of the flexible substrate, over which side edge the protective material layer the flexible substrate is to be folded.

As is shown in FIGS. 1 and 3, the protective layer 9 may also, likewise, be folded over one of the first and second longitudinally separated ends 7, 8 and the folded-over portion of the protective layer material 16 be secured to the second major surface 4 of the flexible substrate 2. Although not shown in the figures, the protective layer material 9 may also, likewise, be folded over both the first and the second longitudinally separated ends 7, 8 and the folded-over portions of the protective layer material be secured to the second major surface 4 of the flexible substrate 2.

In the sensing panel 1 illustrated in FIGS. 1 to 3, the sensing elements 11, 11', 11", 11''' are all disposed on flexible substrate 2 at a distance from the transversally separated longitudinal side edges 5, 6 and the longitudinally separated edges 7,8, i.e. they are arranged distinctly inboard of the perimeter of the flexible substrate 2.

In the sensing panel 1 illustrated in FIGS. 1 to 3, the protective layer 9 is arranged such that its folded-over portions 14, 15, 16 are not superimposed on the sensing elements 11, 11', 11", 11'''. i.e. no part of the folded-over portions 14, 15, 16 of the flexible protective layer 9 covers any part of the sensing elements 11, 11', 11", 11'''.

The nearest distance from the longitudinally extending side edges 5, 6 of the flexible substrate 2 to the transversally outermost edge of the sensing elements nearest to that side edge may be from 1, 2, 3 or 4 to 10, 8 or 6 mm.

Materials suitable for the protective layer 9 are able to be folded over an edge of the flexible substrate, and are self-supporting materials, typically in the form of a web, a tape or a film.

The protective layer 9 may be secured to the flexible substrate by any means suitable. For instance, the protective layer material may in itself be a self-adhering adhesive tape or it may be a non-adhering layer adhered to the flexible substrate by means of an adhesive.

Materials suitable for the flexible protective layer 9 are such materials that when attached to the flexible substrate 2 they protect the flexible substrate 2 and the sensing elements 11, 11', 11", 11''' disposed thereon from damage, such as providing protection against water, and dirt. For that purpose, suitable materials may be substantially liquid impermeable permeable. They may also provide a mechanical resistance e.g. against scratching to the surface of the substrate.

Further, materials suitable for the protective layer 9 may provide a soft, rounded edge to the sensing panel 1 when folded over edges of the flexible substrate 2. For that purpose, suitable materials may have a thickness of at least 0.1 mm, such as from 0.1, 0.2 or 0.3 to 1, 0.8 or 0.5 mm. The protective layer material 9 may have a basis weight of from 50, such as from 100, to 300, such as to 200 $g/m^2$.

Further, materials suitable for the protective layer 9 may provide a soft, skin friendly appearance to the sensing panel 1. For that purpose, suitable materials may be of a slightly compressible nature, such a foam material.

One example of a suitable material for the protective layer 9 is Dermabak® F110 from Rogers Corporation, being a poly urethane-based foam membrane with a thickness of about 0.4 mm and a basis weight of about 200 g/m$^2$, which can be secured to the flexible substrate 2 by means of e.g. a pressure sensitive adhesive.

The protective layer 9 need not cover the complete first major surface 3 of the flexible substrate 2, as there may be areas that does not benefit from and/or are not compatible with the protective layer 9, such as for instance areas of the sensing panel that constitute a logger unit attachment area. However, it may be beneficial that at least 50, 60, 70, 80 or 90% of the first major surface 3 is covered by the flexible protective layer. 100% coverage is also within the scope of the present disclosure Likewise, the protective layer 9 does not need to be folded over the full length of the longitudinally extending side edges of 5, 6 of the flexible substrate, as there may be portions of these that does not benefit and/or are not compatible with the presence of the folded-over portions 14, 15. However, it may be beneficial that from 50, 60, 70 or 80, to 100, 95 or 90% of each one of longitudinally extending side edges 5, 6 are positioned with the respective folds 12, 13 of the protective layer 9.

The fastening means layer 10 is disposed on and secured to the second major surface 4 of the flexible substrate 2. The fastening means layer 10 is, as is illustrated in FIG. 4, intended to enable the sensing panel 1 to be attached on an exterior surface, in this case, the exterior, garment facing surface 31 of a hygiene absorbent article 30 with the second major surface 4 of the flexible substrate facing towards the garment facing surface of 31 of the hygiene absorbent article. The fastening material layer may attach to the intended surface by means of mechanical fastening elements, such as hook or loops of a hook and loop combination, or by means of and adhesive. The fastening means layer 10 also serves to protect the second major surface 4 of the flexible substrate 2, the sensing elements 11, 11', 11", 11'" and optionally other components and may, for that purpose, be liquid impermeable.

The garment facing surface 31 of hygiene absorbent articles 30 are conventionally of a fibrous nonwoven material, and the fastening material layer may in such cases utilize hooks as fastening elements. Hook materials are readily available from commercial sources such as 3M and Velcro.

Together with the folded-over portions 14, 15, 16 of the protective layer material 9, the fastening means layer 10 may substantially completely cover the full second major surface 4 of the flexible substrate 3.

As illustrated in FIGS. 2 and 3, the fastening material layer 10 may be arranged extending partly on top of and covering at least part of the folded-over portions 14, 15, 16 of the protective layer 9, i.e. such that the folded-over portions 14, 15, 16 are at least partly disposed between the flexible substrate 2 and the fastening means layer 10.

Such overlapping configuration provides a relatively secure seal while also enabling a large fastening effective area of the fastening layer material 10.

A flexible sensing panel 1 with the protective layer 9 and the fastening means layer 10 arranged around the flexible substrate as described herein provides a good resistance against the formation of permanent creases and folds in the flexible sensing panel. Such creases and folds may impair the function of the sensing panel and render the sensing panel a worn-out visual appearance, and a good resistance against this may increase the life-time of the sensing panel and a reduces material consumption.

The flexible sensing panel 1 according to the present disclosure is intended to be used in a hygiene monitoring device, which is able to monitor the hygiene status of absorbent hygiene article, such as a diaper, an incontinence pad or a sanitary napkin, for example by detecting the presence of and/or determining the amount of body liquids, such as feces, urine, blood and/or menstrual fluid, absorbed by the absorbent hygiene article.

The flexible sensing panel 1 may itself house necessary electronic components, such as for example a power source for operating the sensing elements 11, 11', 11", 11'" and a transmitter for transmitting the output from the sensing elements to an intended receiver of such output.

Alternatively, and as illustrated in the FIGS. 1 to 4, the sensing panel 1 is connectible to a data logger unit 21 by means of a connector means 17 disposed on the first major surface of the sensing panel 1, where the data logger unit 21 comprises the necessary electronic components. When the data logger unit 21 is operatively connected to the sensing panel 1, the data logger is able to operate the sensing elements 11, 11', 11", 11'" and to transmit the output from these sensing elements to the intended receiver of such output.

The connector means 17 is schematically illustrated in the FIGS. 1 and 3 and may be a single connector enabling both physical attachment and electrical contact between the data logger unit 21 and the flexible sensing panel, or may be a combination of means for physical attachment and means for electrical connection. For example, the means for electrical connection may be a male-female connector combination, such as a mezzanine connector combination with male connector on the data logger unit 21 and the female connector on the flexible sensing panel 1, or vice versa. Such mezzanine connector may also double as the means for physical attachment, or alternatively the physical attachment may be strengthened by an interlocking design of the data logger unit 21 and the sensing panel 1.

When the data logger unit 21 is removably attachable to the sensing panel 1, this enables the data logger 21 to be removed from the sensing panel 1 and placed on a different sensing panel as appropriate, for example is the first sensing panel 1 is ultimately worn out and needs to be discarded, or if the it needs to be cleaned before further use.

In the illustrated sensing panel 1, four (4) sensing elements 11, 11', 11", 11'" in the form of conductive plates are disposed on the flexible substrate, with conductive leads (not shown) connecting the respective sensing element with the connector means 17 and the data logger unit 21 is adapted to measure an impedance value between two sensing elements at a time in order to detect a change in the impedance value indicative of a change in the amount of urine absorbed by the absorbent hygiene article. The present disclosure is however not limited to this specific type of sensing elements, and the at least one sensing element may, in addition or alternatively, represent different types of sensors, such as temperature sensors, VOC sensors or other sensors known to those skilled in the art that may be useful for the purpose of monitoring the hygiene status in a absorbent hygiene article while being arranged on the exterior surface of the absorbent hygiene article.

The invention claimed is:

1. A flexible sensing panel for a hygiene monitoring device, comprising a flexible substrate extending along a longitudinal direction and a transversal direction and having first and second mutually opposite major surfaces in the plane of the longitudinal and transversal direction, first and second mutually opposite, longitudinally extending and transversally separated side edges, and first and second mutually opposite, longitudinally separated ends, the flexible substrate being at least partly disposed between a protective layer and a fastening layer, and at least one sensing element being disposed on the flexible substrate, wherein the protective layer is disposed on and secured to the first major surface of the flexible substrate and is folded over the first and second longitudinally extending side edges onto the second major surface of the flexible substrate and secured thereto to position at least part of the first and second longitudinally extending side edges within the so formed folds, and wherein the fastening layer is at least partly disposed on the second major surface of the flexible substrate and secured thereto.

2. The flexible sensing panel according to claim 1, wherein the protective layer disposed on and secured to the first major surface of the flexible substrate is folded over at least one of the first and second longitudinally separated ends of the flexible substrate onto the second major surface thereof and secured thereto.

3. The flexible sensing panel according to claim 1, wherein the folded-over portions of the protective layer and the fastening layer together covers the full second major surface of the flexible substrate.

4. The flexible sensing panel according to claim 1, wherein the first and second longitudinally extending side edges are positioned within the folds along at least 50% of their extension in the longitudinal direction.

5. The flexible sensing panel according to claim 1, wherein the at least one sensing element is disposed at a distance from the longitudinally extending, transversally separated side edges and optionally from the longitudinally separated edges, and wherein the folded over-portions of the protective layer are not superposed on the at least one sensing element.

6. The flexible sensing panel according to claim 1, wherein said folded-over portions of the protective layer is at least partly disposed between the fastening layer material and the flexible substrate.

7. The flexible sensing panel according to claim 1, wherein the protective layer is secured to the flexible substrate by an adhesive.

8. The flexible sensing panel according to claim 1, wherein the protective layer is made from a liquid impermeable material.

9. The flexible sensing panel according to claim 1, wherein the protective layer is a foam material.

10. The flexible sensing panel according to claim 1, wherein the protective layer has a thickness of from 0.1 to 1 mm.

11. The flexible sensing panel according to claim 1, wherein the protective layer has basis weight of from 100 to 300 g/m2.

12. The flexible sensing panel according to claim 1, wherein said fastening layer comprises mechanical fasteners disposed on a backing layer.

13. The flexible sensing panel according to claim 12, wherein said mechanical fasteners are hooks.

14. The flexible sensing panel according to claim 1, comprising at least two longitudinally or transversally spaced-apart sensing elements.

15. The flexible sensing panel according to claim 1, wherein the flexible sensing panel is elongate along the longitudinal axis.

16. The flexible sensing panel according to claim 1, wherein the ratio of the longitudinal length to the transversal width of the flexible sensing panel is 5:1 or higher.

17. The flexible sensing panel according to claim 1, wherein a data logger unit or a connector for removable attachment of data logger unit is disposed on a portion of the first major surface of the flexible sensing panel, and wherein the data logger unit and connector for removable attachment of the data logger unit is electrically connected to said at least one sensing element.

18. The flexible sensing panel according to claim 1, adapted for being secured to a garment facing surface of an absorbent hygiene article by the fastening means layer.

19. A hygiene monitoring device, comprising a flexible sensing panel according to claim 1, and a data logger unit removably attachable to the sensing panel and electrically connectible to the sensing elements adapted for detecting the presence of or quantifying the amount of body fluids absorbed by a absorbent hygiene article with which the hygiene monitoring device is associated.

20. The flexible sensing panel according to claim 1, adapted for being removably secured to a garment facing surface of an absorbent hygiene article by means of the fastening means layer.

\* \* \* \* \*